(12) United States Patent
Cottet et al.

(10) Patent No.: US 9,689,786 B2
(45) Date of Patent: Jun. 27, 2017

(54) METHOD FOR DETERMINING THE SIZE DISTRIBUTION OF A MIXTURE OF PARTICLES USING TAYLOR DISPERSION, AND ASSOCIATED SYSTEM

(71) Applicants: CENTRE NATIONAL DE LA RECHERCHE SCIENTIFIQUE (C.N.R.S), Paris (FR); UNIVERSITE MONTPELLIER I, Montpellier (FR); UNIVERSITE MONTPELLIER 2, SCIENCES ET TECHNIQUES, Montepellier (FR)

(72) Inventors: Hervé Cottet, Le Cres (FR); Luca Cipelletti, Montpellier (FR); Michel Martin, Le Plessis-Pâté (FR); Jean-Philippe Biron, Saint Gely du Fesc (FR)

(73) Assignees: CENTRE NATIONAL DE LA RECHERCHE SCIENTIFIQUE (C.N.R.S.), Paris (FR); UNIVERSITE MONTPELLIER 1, Montpellier (FR); UNIVERSITE MONTPELLIER 2, SCIENCES ET TECHNIQUES, Montpellier (FR)

( * ) Notice: Subject to any disclaimer, the term of this patent is extended or adjusted under 35 U.S.C. 154(b) by 321 days.

(21) Appl. No.: 14/410,019

(22) PCT Filed: Jun. 26, 2013

(86) PCT No.: PCT/EP2013/063432
§ 371 (c)(1),
(2) Date: Dec. 19, 2014

(87) PCT Pub. No.: WO2014/001409
PCT Pub. Date: Jan. 3, 2014

(65) Prior Publication Data
US 2015/0192507 A1 Jul. 9, 2015

(30) Foreign Application Priority Data

Jun. 26, 2012 (FR) ..................................... 12 56050

(51) Int. Cl.
*G01N 31/00* (2006.01)
*G01N 15/02* (2006.01)
*G01N 35/08* (2006.01)

(52) U.S. Cl.
CPC ....... *G01N 15/0205* (2013.01); *G01N 35/085* (2013.01); *G01N 15/02* (2013.01); *G01N 15/0211* (2013.01)

(58) Field of Classification Search
CPC ............... G01N 15/02; G01N 15/0211; G01N 15/0205; G01N 27/447; G01N 27/44726
(Continued)

(56) References Cited

U.S. PATENT DOCUMENTS 7,099,778 B2 * 8/2006 Chien .................... G01N 13/00
422/110
8,118,986 B2 * 2/2012 Cottet .................. G01N 27/447
204/450
2011/0264380 A1 10/2011 Cottet et al.

OTHER PUBLICATIONS

Cottet, et al. 2007 "Determination of dendrigraft poly-L-lysine diffusion coefficients by Taylor dispersion analysis" *Biomacromolecules*, 8(10); 3235-3243.
(Continued)

*Primary Examiner* — An Do
(74) *Attorney, Agent, or Firm* — Knobbe, Martens, Olson & Bear, LLP

(57) ABSTRACT

A method for determining the size distribution of a mixture of molecule or particle species including the steps of: injecting a sample of the mixture to be analyzed inside a capillary in which an eluent is flowing; transporting the sample injected along the capillary from an injection section to a detection section thereof, in experimental conditions
(Continued)

suitable to generate a Taylor dispersion phenomenon that is measurable at the level of the detection section; generating, by a suitable sensor included in the detection section, a signal characteristic of the Taylor dispersion of the transported sample; processing the detection signal in order to obtain an experimental Taylor signal S(t); and analyzing the experimental Taylor signal Ŝ(t), wherein the step of analyzing an experimental Taylor signal Ŝ(t) of a sample of the mixture consists of searching an amplitude distribution $P(G_{(c)})$ that allows the experimental Taylor signal Ŝ(t)' to be broken down into a sum of Gaussian functions.

15 Claims, 4 Drawing Sheets

(58) Field of Classification Search
USPC .................. 702/22, 23, 25, 29; 204/450–452
See application file for complete search history.

(56) References Cited

OTHER PUBLICATIONS

Cottet, et al. 2007 "Taylor dispersion analysis of mixtures" *Analytical Chemistry* 79(23); 9066-9073.

Kelly, B. and Leaist, D.G. 2004 "Using Taylor dispersion profiles to characterize polymer molecular weight distributions" *Physical Chemistry Chemical Physics* 6(24); 5523-5530.

Schure, 1999 "Advances in the theory of particle size distributions by field-flow fractionation—outlet and apparent polydispersity at constant field" *Journal of Chromatography* 831(1); 89-104.

* cited by examiner

METHOD FOR DETERMINING THE SIZE DISTRIBUTION OF A MIXTURE OF PARTICLES USING TAYLOR DISPERSION, AND ASSOCIATED SYSTEM

FIELD OF THE INVENTION

This invention concerns methods for determining the size distribution of a mixture of particles by implementing the Taylor dispersion and associated system, including the following steps:

- injecting a sample of the mixture to be analyzed inside a capillary in which an eluent is flowing;
- transporting the sample injected along the capillary from an injection section to a detection section thereof, in experimental conditions suitable to generate a Taylor dispersion phenomenon that is measurable at the level of the detection section;
- generating, by means of a suitable sensor included in the detection section, a signal characteristic of the Taylor dispersion of the transported sample;
- acquiring the detection signal in order to obtain an experimental Taylor signal; and
- analysing the experimental Taylor signal.

Below, 'particle' refers to any molecule in solution and/or particles in suspension in the mixture.

In this document, a species includes all particles characterized by the same size, e.g., the same hydrodynamic ray. A species is thus associated with a 'particle size' value.

BACKGROUND OF THE INVENTION

In this field, the 'deconvolution' of a Taylor signal refers to the processing of the experimental Taylor signal leading to the determination of the hydrodynamic ray of each of the species forming the mixture and the determination of the concentration of each of these species.

The international application published under no. WO 2010 009907 A1 discloses a method of the aforementioned type, the analysis step of which implements various deconvolution algorithms for an experimental Taylor signal. However, these algorithms may only be used in the specific case of a binary mixture, i.e., a mixture of two species. Accordingly, these known algorithms do not allow for the analysis of any desired sample, but only of samples of which it is known in advance that they result from the mixture of two species.

SUMMARY OF THE INVENTION

In practice, it is currently considered impossible to solve the general problem of deconvoluting the experimental Taylor signal of a sample of any given mixture of species.

The invention thus seeks to alleviate this problem by proposing, in particular, a method for real-time analysis of an experimental Taylor signal of a sample of any given mixture.

To this end, the invention concerns a method for determining the size distribution of a mixture of molecule or particle species including the following steps:

- injecting a sample of the mixture to be analyzed inside a capillary in which an eluent is flowing;
- transporting the sample injected along the capillary from an injection section to a detection section thereof, in experimental conditions suitable to generate a Taylor dispersion phenomenon that is measurable at the level of the detection section;
- generating, by means of a suitable sensor included in the detection section, a signal characteristic of the Taylor dispersion of the transported sample;
- processing the detection signal in order to obtain an experimental Taylor signal $\hat{S}(t)$; and
- analysing (200) the experimental Taylor signal $\hat{S}(t)$, characterized in that the step of analysing an experimental Taylor signal $\hat{S}(t)$ of a sample of the mixture consists of searching an amplitude distribution $P(G_{(c)})$ that allows the experimental Taylor signal $\hat{S}(t)$ to be broken down into a sum of Gaussian functions by means of the equation:

$$\hat{S}(t) = \int_0^\infty P(G_{(c)}) G_{(c)}^{c/2} \exp[-(t-t_0)^2 G_{(c)}^c] dG_{(c)}$$

where t is a variable upon which the experimental Taylor signal depends and $t_0$ is a value of the variable t common to the various Gaussian functions and corresponding to the peak of the experimental Taylor signal $\hat{S}(t)$;

$G_{(c)}$ is a characteristic parameter of a Gaussian amplitude function $P(G_{(c)})$ and is associated:

where c=1, with the diffusion coefficient D of a species according to the relation $$G_{(1)} = 12D/(R_c^2 t_0)$$

for c=−1, to the hydrodynamic ray $R_h$ of a species according to the relation $$G_{(-1)} = \frac{2k_B T}{\pi \eta R_c^2 t_0} R_h^{-1};$$

and for c=−1/$d_f$=−(1−a)/3, to the molar mass M of a species according to the relation $$G = \frac{2k_B T}{\pi \eta R_c^2 t_0} \left(\frac{10\pi N_a}{3K}\right)^{1/3} M^{-\left(\frac{1+a}{3}\right)},$$

where $k_B$ is the Boltzmann constant, T is the absolute temperature expressed in Kelvins at which the experiment is conducted, η is the viscosity of the eluent used, $R_c$ is the internal ray of the capillary used, $N_a$ is Avogadro's number, and K and a are Mark Houwink coefficients, by implementing a constrained regularization algorithm consisting of minimising a cost function $H_\alpha$ including at least one constraint term associated with a constraint that must observe the amplitude distribution $P(G_{(c)})$ that is the solution of the foregoing equation, whereby the minimization is carried out on an interval of interest of the values of the parameter $G_{(c)}$.

According to specific embodiments, the method includes one or more of the following characteristics, taken alone or in all combinations technically possible:

- the foregoing equation is discretized by subdividing the interval of values of the parameter $G_{(c)}$, whereby each discretization point $G_m$ is indexed by an integer m that varies between the unit value and the value N, whereby the point $G_m$ is at a distance from the point $G_{m-1}$ corresponding to a sub-interval of the length $c_m$;
- the cost function takes the form:

$$H_\alpha = \chi^2 + \alpha^2 \Delta^2$$

Where:
the first term $\chi^2$ is a distance term between the experimental Taylor signal $\hat{S}(t)$ and a reconstructed Taylor signal defined by:

$$S(t)=\sum_{m=1}^{N} c_m P(G_m)\sqrt{G_m}\exp[-(t-t_0)^2 G_m], \text{ and}$$

the second term $\Delta^2$ is a constraint term associated with the at least one constraint that must observe the amplitude distribution P(G) that is the solution of the foregoing equation, whereby the second term is introduced by a Lagrange coefficient $\alpha$, allowing the contribution of the second term of the cost function $H_\alpha$ to be adapted to the first term;
the first term $\chi^2$ is a distance of the type 'least squares' taking the form:

$$\chi^2=\sum_{k=1}^{L}(S'(t_k)-\hat{S}(t_k))^2$$

where the experimental Taylor signal $\hat{S}(t)$ and the reconstructed function S'(t) are sampled over time, whereby each sample is indexed by an integer k varying between the unit value and the value L;
the at least one constraint that must be observed by the amplitude distribution P(G) that is the solution of the foregoing equation is a regularity constraint associated with a constraint term $\Delta^2$ preferably taking the form:

$$\Delta^2=\sum_{m=2}^{N-1}[P(G_{m-1})-2P(G_m)+P(G_{m+1})]^2;$$

the analysis step includes a step of determining the optimal value $\alpha_0$ of the Lagrange coefficient $\alpha$ such that the value of the distance term $\chi^2$ corresponding to the minimum of the cost function $H_{\alpha=\alpha_0}$ is close by values lower than a statistical error $\nu$, preferably of the form $\nu=L-N$;
because the interval of interest of the values of the parameter $G_{(c)}$ are delimited by a minimum $G_m$ in and a maximum $G_{max}$, the method includes a step of determining the values of the minimum and maximum;
it includes a step of breaking down a normalized Taylor signal s(t) associated with the experimental Taylor signal $\hat{S}(t)$ into components by the relation: $s(t)=S(t)/S(t_0)$, consisting of adjusting to the curve ln [s(t)] a second-order polynomial of the variable $(t-t_0)^2$ so as to determine the first-order components $\Gamma_1$ and second-order components $\Gamma_2$, and in that the step of determining the values of the minimum $G_{min}$ and maximum $G_{max}$ uses the equations:

$$\beta = \ln\Gamma_1 - \ln\left(1 + \frac{\Gamma_2}{\Gamma_1^2}\right) \text{ and } \gamma = \sqrt{\ln\left(1 + \frac{\Gamma_2}{\Gamma_1^2}\right)}$$

where $\beta$ and $\gamma$ are respectively the average and the standard deviation of the logarithm of the parameter G of a log-normal distribution, followed by, $$G_{min}=\exp(\beta-k\sqrt{2}\gamma) \text{ and } G_{max}=\exp(\beta+k\sqrt{2}\gamma);$$

the step of determining the values of the minimum and maximum of the interval of interest is empirical and consists of:
determining a normalized Taylor signal s(t) associated with the experimental Taylor signal $\hat{S}(t)$ by the relation: $s(t)=S(t)/S(t_0)$,
calculating the logarithm ln [s(t)],
determining the derivative $$\frac{\partial \ln s}{\partial x}$$

relative to the variable $x=(t-t_0)^2$, and
determining the values of the parameters $\tau_{min}$ and $\tau_{min}$ related to the extrema of the derivative according to the relations:

$$\tau_{min} = a_{min}\left(\left|\frac{\partial \ln s}{\partial x}\right|_{max}\right)^{-1/2}$$

$$\tau_{max} = a_{max}\left(\left|\frac{\partial \ln s}{\partial x}\right|_{min}\right)^{-1/2}$$

with $\alpha_{min}=0.1$; $\alpha_{max}=3$,
determining the minimum $G_{min}$ and maximum $G_{max}$ using the equations:
for $c=1$: $G_{min}=\tau_{max}^{-2}, G_{max}=\tau_{min}^{-2}$,
for $c=-1$: $G_{min}=\tau_{min}^{-2}, G_{max}=\tau_{max}^{-2}$,
for $c=-1/d_f=-(1+a)/3$:

$$G_{min} = \tau_{min}^{\left(\frac{6}{1+a}\right)}, G_{max} = \tau_{max}^{\left(\frac{6}{1+a}\right)};$$

it includes a step of measuring an average in T, $\langle G \rangle_T$, of the parameter $G_{(1)}$ based on the experimental Taylor signal and/or an average in $\Gamma$, $\langle G \rangle_\Gamma$, of the parameter $G_{(1)}$ based on the breakdown, whereby each average may be used in a constraint that must be observed by the amplitude distribution $P(G_{(1)})$ that is the solution of the foregoing equation;
the step of determining the values of the minimum $G_{min}$ and maximum $G_{max}$ uses the equations:

$$\beta = \frac{1}{3}\ln\langle G\rangle_\Gamma + \frac{2}{3}\ln\langle G\rangle_T$$

$$\gamma = \sqrt{\frac{2}{3}\ln\frac{\langle G\rangle_\Gamma}{\langle G\rangle_T}}$$

then
$G_{min}=\exp(\beta-k\sqrt{2}\gamma)$ and $G_{max}=\exp(\beta+k\sqrt{2}\gamma)$.

The invention also concerns a data storage medium including instructions for the execution of a method for determining the hydrodynamic ray, diffusion coefficient, or molar mass distribution of a mixture of molecule or particle species as defined above when the instructions are executed by a computer.

The invention lastly concerns a system for determining the hydrodynamic ray, diffusion coefficient, or molar mass distribution of a mixture of molecule or particle species including a computer, whereby the computer is programmed to execute a method for determining the hydrodynamic ray, diffusion coefficient, or molar mass distribution of a mixture of molecule or particle species as defined above.

BRIEF DESCRIPTION OF THE DRAWINGS

Other characteristics and advantages of the invention will become apparent from the following detailed description, provided by way of example and by reference to the attached drawings, in which:

FIG. 3 shows the accumulation of three repetitions of the experimental Taylor signal; FIG. 4 shows the hydrodynamic ray distribution obtained by implementing the method of FIG. 2 compared with that obtained by steric exclusion chromatography and provided by the supplier of the synthetic polymer samples; and FIG. 5A shows the adjustment of the Taylor signal by the method of FIG. 2, and FIG. 5B shows the breakdown of the experimental Taylor signal of FIG. 3 into its components.

DETAILED DESCRIPTION OF THE PREFERRED EMBODIMENT

Experimental Device

Figure 1:
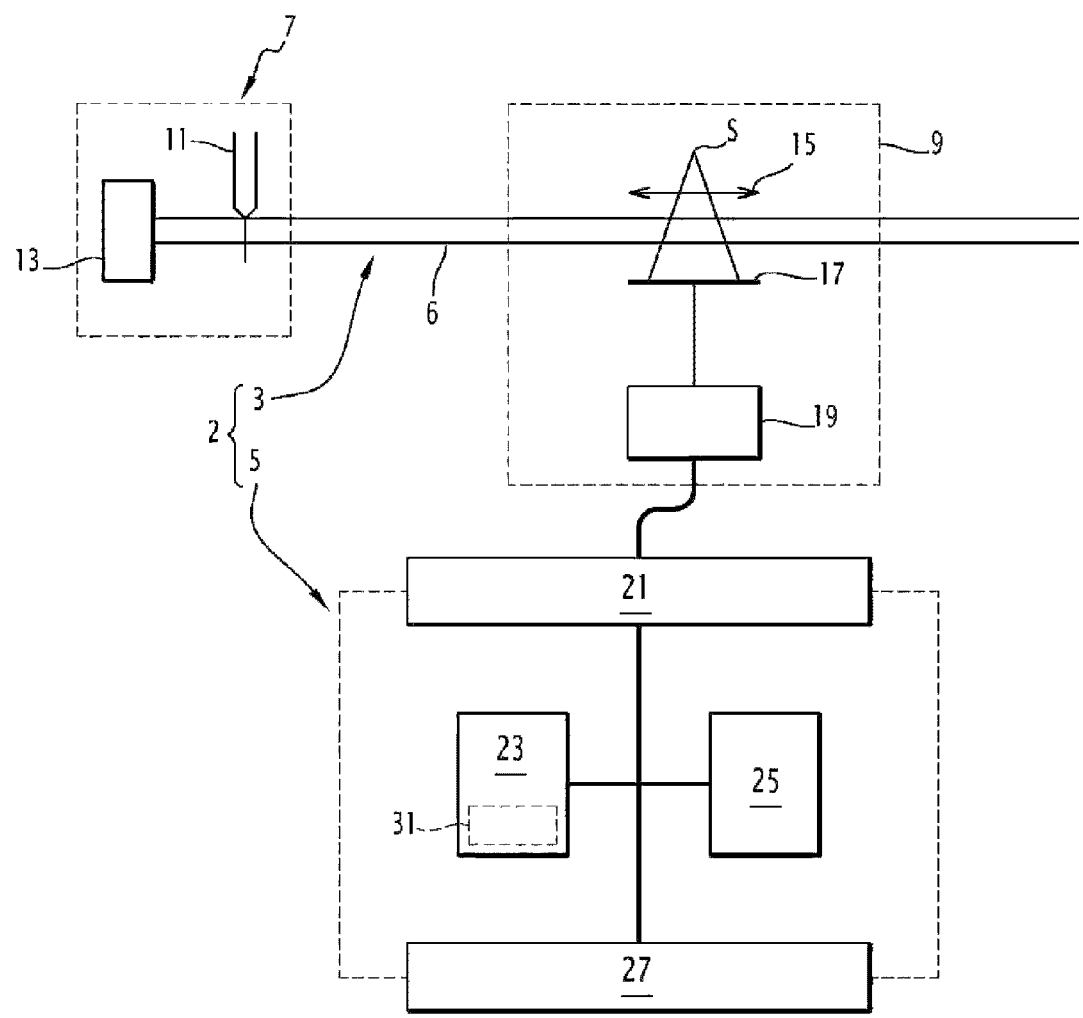
FIG. 1 is a schematic representation of a system for determining the size distirbution of a particle mixture.

By reference to FIG. 1, the system for determining the size of a mixture of particles 2 includes an experimental device 3 suited to generate a Taylor dispersion phenomenon and to generate an experimental Taylor signal, and an analysis device 5 suited to analyse the experimental Taylor signal output by the experimental device 3 in order to determine in real time the size distribution of the particle mixture, a sample of which was injected into the experimental device.

The experimental device 3 includes, as is known, a capillary 6.

The experimental device 3 includes, in the vicinity of one end of the capillary 6, an injection section 7, and, in the vicinity of the other end of the capillary 6, a detection section 9.

The injection section 7 includes means 11 for injection into the capillary 6 of a sample of the mixture to be analyzed. The injection section 7 also includes means to allow an eluent to flow inside the capillary 6 from the injection section 7 to the detection section 9. These flow means are shown schematically in FIG. 1 by block 13.

The detection section 9 is optical. It is equipped with an optical cell including a light source S and an optical system 15 suited to cause the rays of light emitted by the source S to converge on a narrow portion of the capillary 6. Along the optical axis of the optical system 15, but opposite the lighted side of the capillary 6, the cell includes a CCD, diode array, or photomultiplier sensor 17 suited to collect the light that has passed through the capillary 6 and to generate a detection signal corresponding to the light collected. The sensor 17 is electrically connected to an electronic card 19 for pre-processing and digitising the detection signal generated by the sensor 17. The card 19 outputs a digital measurement signal that is time-dependent. This measurement signal is referred to as the 'experimental Taylor signal' or Taylor-gram. It is indicated by the notation $\hat{S}(t)$ in the following. It depends on the time t.

The experimental Taylor signal $\hat{S}(t)$ is sampled at a predetermined temporal frequency, although the sampling points $t_k$ (k=1, ..., L) are at regular intervals. The experimental Taylor signal $\hat{S}(t)$ thus consists of a group of L pairs of data $(t_k, \hat{S}(t_k))$.

In one variant, the detection section may be of another type, e.g., a conductivity detector, using mass spectrometry, fluorescence (laser-induced, if applicable), electrochemical, light diffusion, or more generally, any type of detector used in capillary electrophoresis. In particular, the Taylor signal may not be a time signal (scrolling the Taylor peak in front of a narrow sensor), but rather a spatial signal (instantaneous capture of the Taylor peak in front of an extended sensor). In this case, the variable t does not represent time, but the position along the capillary.

The analysis device 5 consists of a computer including an input/output interface 21 to which the electronic card 19 of the experimental device 3 is connected.

The computer further includes a memory 23, such as a RAM and/or ROM, as well as a processing unit 25, such as a microprocessor. The computer also includes human-machine interface means, indicated by the number 27 in FIG. 1. They include, e.g., a touch screen allowing a user to interact with the computer 5. All of the components of the computer are interconnected in a known fashion, e.g., by a data exchange bus.

The experimental Taylor signal $\hat{S}(t)$ is processed by a software application, the instructions of which are stored in the memory 23 and executed by the processing unit 25. This software is shown schematically in FIG. 1 by block 31.

Modelling of the Taylor Signal

In the known manner, assuming that i) the contribution of the diffusion along the axis of the capillary 6 to the dispersion at the level of the peak of the signal is negligible, ii) the injection time of the sample into the capillary 6 is sufficiently short (typically, the injected volume is less than 1% of the volume of the capillary), and iii) the detection device is sensitive to the mass of the molecules, the real Taylor signal S(t) of a monodispersed sample, i.e., a sample having only one species, and, accordingly, characterized by a hydrodynamic ray value $R_h$, or diffusion coefficient D, is modelled by a Gaussian function:

$$S(t) = CM\rho\sqrt{D}\exp[-(t-t_0)^2 12D/(R_c^2 t_0)] + B. \quad (1.)$$

Where:
C is an instrumental constant,
M is the molar mass of the species,
$\rho$ is the molar concentration of the species,
$R_c$ is the internal ray of the capillary,
$t_0$ is the moment corresponding to the peak of the Taylor signal, and
B is an offset constituting a measurement artifact (this term will be omitted in the following for clarity and because it is taken into account in the constrained regularization method).

It should be emphasized that assumption iii) depends on the nature of the sensor used in the detection section, and that the use of another type of sensor results in modifications to the equations shown herein in a manner known to persons skilled in the art.

The real Taylor signal S(t) of a polydispersed sample, i.e., a sample including several species, is modelled for the sum of the contributions of each of the species. Thus, assuming a mixture including a continuum of species, equation (1) is generalized by a continuous sum of Gaussian functions according to:

$$S(t) = \int_0^\infty CM(D)\rho(D)\sqrt{D}\exp[-(t-t_0)^2 12D/(R_c^2 t_0)]dD, \quad (2.)$$

In equation (2), the Gaussian functions are all centred on the same reference time $t_0$.

The parameter $G=12D/(R_C^2 T_0)$ is introduced, causing the equation (2) to become:

$$S(t) = \int_0^\infty P(G)\sqrt{G}\exp[-(t-t_0)^2 G]dG \quad (3.)$$

where P(G) is referred to in the following as the 'amplitude distribution' of the Guassian functions of the parameter G.

A value of the parameter G is associated, via the diffusion coefficient D, with a species. For example, the Stokes-Einstein-Sutherland formula allows for the association of a value of the parameter G with the species characterized by the hydrodynamic ray $R_h$, according to the relation:

$$G = \frac{2k_B T}{\pi \eta R_c^2 t_0 R_h} \quad (4.)$$

Where:
$k_B$ is the Boltzmann constant,
T is the absolute temperature expressed in Kelvins at which the experiment is carried out, and
$\eta$ is the viscosity of the eluent used.

Thus, in equation (3), each Gaussian function $P(G)\sqrt{G}\exp[-(t-t_0)^2 G]$ represents the contribution of one species to the total amplitude of the real Taylor signal S(t). The amplitude P(G) of each Gaussian function depends directly on the concentration of the corresponding species in the mixture.

The function of the software 31 is to determine the distribution P(G) that is the solution of the following equation corresponding to equation 83) when the real Taylor signal S(t) is replaced with the experimental Taylor signal $\hat{S}(t)$:

$$\hat{S}(t) = \int_0^\infty P(G)\sqrt{G}\exp[-(t-t_0)^2 G]dG \quad (5.)$$

Measurement Error Introduced by the Experimental Device

Like any measurement device, the detection section 9 introduces a systematic measurement error such that the experimental Taylor signal $\hat{S}(t)$ is not exactly equal to the real Taylor signal S(t).

The solution of the equation (5) then results in the determination of several distributions that are each solution to the measurement error. In other words, the solution of the equation (5) results in the identification of several families of Gaussian functions that each result in sum in a reconstructed Taylor signal $\hat{S}(t) = \int_0^\infty P(G)\sqrt{G}\exp[-(t-t_0)^2 G]dG$ that is adjusted to the experimental Taylor signal $\hat{S}(t)$, with the adjustment criterion taking into account the measurement error introduced by the detection section.

However, amongst the various distributions P(G) that are solutions to the equation (5), only some have physical significance. It is such a 'physical' solution that the software 31 is suited to determine.

Method for Determining the Physically Significant Distribution

To solve this problem, the software 31 uses an algorithm that implements a constrained regularization method.

This algorithm is based on the following equation, which results from a discretization relative to the parameter G of the equation (5):

$$\hat{S}(t) = \sum_{m=1}^{N-1} c_m P(G_m)\sqrt{G_m}\exp[-(t-t_0)^2 G_m] \quad (6.)$$

where the interval of the values of interest of the parameter G, between the predetermined minimum $G_{min}=G_0$ and maximum $G_{max}=G_N$, is subdivided into N sub-intervals identified by the integer m of the length $c_m$. Preferably, the various sub-intervals have the same length:

$$c_m = \frac{G_N - G_0}{N}$$

The limits are such that the interval on which equation (6) is discretized exceeds the interval for which the distribution P(G) is not nil. Accordingly, $P(G_1) = P(G_N) = 0$.

The unknowns of equation (6) consist of all amplitudes $P(G_m)$, m=1, ... N.

In principle, the solution of equation (6) is obtained by a process of adjusting the experimental Taylor signal $\hat{S}(t)$ by the reconstructed Taylor signal $\hat{S}(t) = \sum_{m=1}^{N} c_m P(G_m)\sqrt{G_m}\exp[-(t-t_0)^2 G_m]$. That is, for any time $t_k$, $S'(t_k)$ must be as near as possible to $\hat{S}(t_k)$.

In order to obtain robust results that are physically significant, however, it is necessary to take into account all information available on the amplitudes $P(G_m)$ during the adjustment process so as to reject all solutions that are not physically acceptable.

To this end, the constrained regularization algorithm solves equation (6) by minimising a cost function dependent on the N unknown $P(G_m)$ and translating the information available on the amplitudes $P(G_m)$ into constraints.

In the current embodiment, the cost function $H_\alpha$ takes the following form:

$$H_\alpha = \chi^2 + \alpha \Delta^2 \quad (7.)$$

It includes a first term $\chi^2$ corresponding to a 'distance' between the experimental Taylor signal $\hat{S}(t_k)$ and a reconstructed Taylor signal $S'(t_k)$.

For example, this first term is a distance of the type 'least squares':

$$\chi^2 = \sum_{k=1}^{L} (S'(t_k) - \hat{S}(t_k))^2 \quad (8.)$$

Another distance measure may be used, in particular, one that, in the foregoing sum, weights each term by a coefficient wk inversely proportional to the noise affecting the measurement taken at the instant $t_k$.

The cost function $H_\alpha$ includes a second term $\Delta^2$, referred to as the constraint term, expressing a constraint that penalises the amplitudes $P(G_m)$ that have no physical significance.

For example:

$$\Delta^2 = \sum_{m=2}^{N-1} [P(G_{m-1}) - 2P(G_m) + P(G_{m+1})]^2 \quad (9.)$$

In this example, the constraint term corresponds to the sum of the terms elevated to the square of the second derivative of the distribution P(G). The constraint term translates a regularity constraint. The amplitudes $P(G_m)$ that vary too rapidly relative to their neighbours, $P(G_{m-1})$ or $P(G_{m+1})$, are thus penalised.

Another example of a regularity constraint is the following:

$$\Delta^2 = \sum_{m=3}^{N-1} [P(G_{m-2}) - 3P(G_{m-1}) + 3P(G_m) - P(G_{m+1})]^2 \quad (9.)$$

This constraint term corresponds to the sum of the terms elevated to the square of the third derivative of the distribution P(G). The generalization to a regularity constraint based on the n-th derivative ($n \geq 1$) is immediate and can be carried out by a person skilled in the art.

In the following, it is assumed that the regularity constraint used is that of the second derivative of the distribution P(G), eq. (9).

The first and second terms of the cost function $H_\alpha$ have relative contributions that may be adapted by selecting the value of a coefficient $\alpha$, a Lagrange coefficient. This coefficient verifies the size of the constraint term relative to the distance term. If $\alpha$ is very small, the constraint term is negligible. In this case, the minimization of the cost function yields the same result as a simple adjustment to the experimental data. For values of $\alpha$ that are too large, on the other hand, a significant cost is assigned to the constraint on the P(G), and the algorithm will reject the solutions that do not observe the constraint at the risk of preserving a solution that does not properly fit the experimental data.

Supplemental constraints that may be expressed in the form of supplemental equalities or inequalities, or $P(G_m)$ linear inequalities are directly imposed during the search for the minimum of the cost function by limiting the search to the subregions specific to the space of the $P(G_m)$.

For example, the constraint that the amplitudes are positive, $P(G_m) \geq 0 \; \forall m$, is imposed by minimising the cost function only on the half space of the positive amplitudes.

For example, if the value of an average $\langle G \langle$ of the parameter G is determined, a supplemental constraint on the amplitudes $P(G_m)$ that are solutions to the equation (6) is that the amplitudes allow the previously determined average $\langle G \rangle$ to be determined at a deviation $\epsilon$. This constraint is also expressed in the form of $P(G_m)$ linear inequalities.

$$\langle G \rangle - \epsilon \leq \Sigma_{m=1}^{N} P(G_m) G_m \leq \langle G \rangle + \epsilon \tag{11}$$

With, for example: $\epsilon / \langle G \rangle = 5\%$.

Equation 12 may easily be generalized to other types of averages than the arithmetical average:

$$\langle G \rangle = \Sigma_{m=1}^{N} P(G_m) G_m \tag{12}$$

for example the averages $\langle G \rangle_T$ and $\langle G \rangle_\Gamma$ which will be introduced below.

A crucial point is the choice of the coefficient $\alpha$ of the cost function $H_\alpha$ in equation 7. Two strategies may be used to select the coefficient $\alpha$:

A first strategy consists of choosing the greater value $\alpha$ such that the value of the distance term $\chi^2$ does not exceed the statistically expected value that depends on the measurement error and the number of degrees of freedom in the constrained regularization process. Thus, if, for each experimental point, the standard deviation of the measurement error $\sigma_k$ is known, $\alpha$ is selected such that the normalized value $\chi_{norm}^2$ of the distance term $\chi^2$ does not exceed the number of degrees of freedom: $\nu = L - N$, where $\chi_{norm}^2$ is given by the equation:

$$\chi_{norm}^2 = \Sigma_{k=1}^{N} \frac{(S'(t_k) - \hat{S}(t_k))^2}{\sigma_k^2} \tag{10.}$$

If the standard deviation of the noise $\sigma_k$ is not known, an estimated value $\sigma_{est}$ thereof may be determined based on the mean deviation between the experimental data and the best possible adjustment without taking into account the constraint, i.e., that obtained for $\alpha=0$:

$$\sigma_{est}^2 = \frac{1}{N} \Sigma_{k=1}^{N} (S'(t_k)(\alpha=0) - \hat{S}(t_k))^2, \tag{11.}$$

where $S'(t_k)(\alpha=0)$ is the value of the k-th point of the Taylor signal reconstructed based on the amplitudes $P(G_m)$ obtained by minimising only the first term of the cost function $H_{\alpha=0}$.

Once the noise has been estimated, $\alpha$ is selected such that the normalized value $\chi_{norm}^2$ of the distance term $\chi^2$, calculated by replacing $\sigma_k$ with $\sigma_{est}$ in equation 12 does not exceed the number of degrees of freedom: $\nu = L - N$ A second strategy consists of selecting $\alpha$ value for a that gives equal weight to the distance term and the constraint term.

In this case, the parameter $\alpha$ that is retained is the one for which, once the constraint function $H_\alpha$ has been minimized, the result is $\chi^2 = \alpha \Delta^2$.

In practice, the selection of $\alpha$ is made then by scanning a large range of values of the coefficient $\alpha$. For each value of $\alpha$, all amplitudes $P(G_m)$ that minimise the cost function $H_\alpha$ are determined. The corresponding values of $\chi_{norm}^2$, $H_\alpha$ and $P(G_m)$ are recorded. Amongst all of the trials, the Lagrange coefficient $\alpha_0$ having the greatest value such that $\chi_{norm}^2 \leq \nu$ is finally retained.

In order to improve the efficiency of the digital search, the values of $\alpha$ are first scanned on a trial grid with large steps, and then the value of $\alpha$ is refined using a finer grid.

Determining $\langle G \rangle_T$ and $\langle G \rangle_\Gamma$ from an Experimental Taylor Signal Below, two averages of G are presented that may be obtained directly from the experimental Taylor signal.

The T average of the parameter G is defined as follows:

$$\langle G \rangle_T = \frac{\Sigma_{m=1}^{N} c_m P(G_m)}{\Sigma_{m=1}^{N} c_m \frac{P(G_m)}{G_m}} = \frac{1}{[G^{-1}]} \tag{12.}$$

and the $\Gamma$ average of the parameter G is defined as follows:

$$\langle G \rangle_\Gamma = \frac{\Sigma_{m=1}^{N} c_m P(G_m) G_m^{3/2}}{\Sigma_{m=1}^{N} c_m P(G_m) G_m^{1/2}}, \tag{13.}$$

where $c_m$ are those defined in relation to equation (6).

The purpose of determining these averages is twofold:

it allows constraints on the amplitudes $P(G_m)$ to be added during the solution of equation (6);

it allows for an estimation of the average and breadth of the distribution P(G). This information is not only interesting in itself, but also allows for a determination of the interval of the values of the parameter G on which a solution to equation (6) can be sought.

$\langle G \rangle_T$ and $\langle G \rangle_\Gamma$ may be calculated respectively based on the temporal variance of the experimental Taylor signal and based on the cumulative approach described below.

Determining $\langle G \rangle_T$ Based on the Temporal Variance of the Experimental Taylor Signal It is shown that:

$$\frac{\int_0^{+\infty} S(t)dt}{\int_0^{+\infty} S(t)(t-t_0)^2 dt} \approx \frac{\int_{-\infty}^{+\infty} S(t)dt}{\int_{-\infty}^{+\infty} S(t)(t-t_0)^2 dt} = \qquad (14.)$$

$$\frac{\sqrt{\pi}\int_0^{+\infty} P(G)dG}{\frac{\sqrt{\pi}}{2}\int_0^{+\infty} G^{-1}P(G)dG} = 2[\overline{G^{-1}}]^{-1} = 2\langle G \rangle_T$$

Thus, the T average of the parameter G is accessible by integrating the experimental Taylor signal.

With $G = 12D/(R_c^2 t_0)$, the T average of the parameter D is given by:

$$\langle D \rangle_T = \frac{R_c^2 t_0}{24} \frac{\int_0^{+\infty} S(t)dt}{\int_0^{+\infty} S(t)(t-t_0)^2 dt} \qquad (15.)$$

Determining $\langle G \rangle_\Gamma$ Based on a Breakdown of the Experimental Taylor Signal In this part, the breakdown of the experimental Taylor signal is described in the case of a sample that is moderately polydispersed.

It is assumed that the size distribution is discrete. Equation (2) then becomes:

$$S(t) = C\Sigma_{i=1}^N \rho_i M_i \sqrt{D_i} \exp[-(t-t_0)^2 12 D_i/(R_c^2 t_0)] \qquad (16.)$$

where $\eta_i$ is the molar concentration of the i-th species in the mixture, and $M_i$ and $D_i$ are respectively the molar mass and diffusion coefficient thereof.

It is useful to 'normalise' the Taylor signal relative to the height of its peak by introducing:

$$s(t) = S(t)/S(t_0 = \Sigma_{i=1}^N f_i \exp[-(t-t_0)^2 G_i] \qquad (17.)$$

Where:
- $G_i = 12D_i/(R_c^2 t_0)$ and
- $f = \rho_i M_i \sqrt{D_i}/\Sigma_{i=1}^N (\rho_i M_i \sqrt{D})$ is the relative contribution of the i-th species in the Taylor signal. It should be noted that $t_0$ depends on the diffusion coefficient of the i-th species.

The $\Gamma$ average of the parameter G is then expressed as follows:

$$\langle G \rangle_\Gamma \equiv \frac{\sum_{i=1}^N \rho_i M_i \sqrt{D_i} \, G_i}{\sum_{i=1}^N \rho_i M_i \sqrt{D_i}} = \Sigma_{i=1}^N f_i G_i. \qquad (18.)$$

By positing $G_i = \langle G \rangle_\Gamma = \delta G_i$, with $\langle \delta G \rangle_\Gamma = 0$, equation (19) becomes:

$$s(t) = \exp[-(t-t_0)^2 \langle G \rangle_\Gamma]\Sigma_{i=1}^N f_i \exp[-(t-t_0)^2 \delta G_i], \qquad (19.)$$

which is the product of a Gaussian function by correction terms.

If $(t-t_0)^2 \delta G_i \ll 1$, i.e., near the peak of the Taylor signal, the limited development of the second term of equation (21) results in:

$$\exp[-(t-t_0)^2 \delta G_i] = 1 - (t-t_0)^2 \delta G_i + \tfrac{1}{2}[(t-t_0)^2 \delta G_i]^2 + \ldots \qquad (20.)$$

Which leads, in equation (21), using $\Sigma_{i=1}^N f_i = 1$ and $\Sigma_{i=1}^N \delta G_i = 0$ to:

$$s(t) = \exp[-(t-t_0)^2 \langle G \rangle_\Gamma](1 + \tfrac{1}{2}(t-t_0)^4 \langle \delta G^2 \rangle_\Gamma + \ldots ) \qquad (21.)$$

Where the size distribution is not too broad (i.e., a slightly polydispersed sample), it is possible to express the normalized Taylor signal s(t) as the sum of a Gaussian function (as in the case of a monodispersed sample) and correction terms (to take into account a deviation in the case of a monodispersed sample).

Taking the logarithm of the expression (23) and carrying out a new limited development, the following is obtained:

$$\ln [s(t)] = -(t-t_0)^2 \langle G \rangle_\Gamma + \tfrac{1}{2}(t-t_0)^4 \langle \delta G^2 \rangle_\Gamma + \ldots \qquad (22.)$$

The equation (24) is the desired cumulant development.

The coefficients $\Gamma_1 = \langle G \rangle_\Gamma$ and $\Gamma_2 \langle \delta G^2 \rangle_\Gamma$ are the first- and second-order cumulants of this development.

They may be obtained by adjusting a second-order polynomial of the variable $(t-t_0)^2$ to the function $\ln [s(t)]$.

The first cumulant also provides access to the $\Gamma$ average of the diffusion coefficient:

$$\langle D \rangle_\Gamma = \langle G \rangle_\Gamma \frac{R_c^2 t_0}{12} = \Gamma_1 \frac{R_c^2 t_0}{12}. \qquad (23.)$$

The $\Gamma$ average is different to the aforementioned T average because the diffusion coefficient D appears there at different powers. These two averages contain different information on the distribution P(G). They allow for the addition of two constraints in the cost function to be minimized.

The second cumulant is linked to the $\Gamma$ average of the variance of the distribution of the diffusion coefficients, providing an estimate of the polydispersity of the sample. More specifically, the ratio of the second cumulant divided by the square of the first cumulant gives:

$$\frac{\Gamma_2}{\Gamma_1^2} = \frac{\langle \delta G^2 \rangle_\Gamma}{\langle G \rangle_\Gamma^2} = \frac{\langle D^2 \rangle_\Gamma - \langle D \rangle_\Gamma^2}{\langle D \rangle_\Gamma^2} = \frac{\dfrac{\overline{D^{5/2}}}{\overline{D^{1/2}}} - \left(\dfrac{\overline{D^{3/2}}}{\overline{D^{1/2}}}\right)^2}{\left(\dfrac{\overline{D^{3/2}}}{\overline{D^{1/2}}}\right)^2}. \qquad (24.)$$

Selection of the Interval of the Values of the Parameter G on Which to Seek a Solution In the constrained regularization adjustment procedure, the choice of the interval of the values G on which the distribution P(G) is sought is an important factor.

In fact, the number N of points used in the discretization of the equation (6) cannot be too large; otherwise, the calculation time for the adjustment will be too long.

Furthermore, N must be significantly smaller than the number L of digitization points of the experimental Taylor signal.

Typical values of N are in the range of 50-200.

These considerations show that the interval $[G_{min}, G_{max}]$ ($G_{min}=G_0$ and $G_{max}=G_N$) must be carefully chosen.

However, the interval $[G_{min}, G_{max}]$ must be greater than the interval on which the distribution P(G) is not nil in order to avoid artifacts due to the truncation of this distribution.

Additionally, if the interval on which the distribution P(G) is not nil is a sub-interval of the interval $[G_{min}, G_{max}]$ that is too narrow, the details of the distribution P(G) will be weekly resolved during discretization.

It is also essential to define an automatic procedure allowing for the determination of $G_{min}$ and $G_{max}$, such that the user does not waste time selecting the limits of the interval and avoiding a series of trial/error.

We propose three possible approaches to determine $G_{min}$ and $G_{max}$. The first two approaches are based on the calculation of the equivalent log-normal distribution, whilst the third is empirical and based on the representation of ln [S(t)] depending on $(t-t_0)^2$ in the same system of axes that is used for the breakdown into cumulants.

Determination of the Interval Based on a Log-Normal Distribution

Equivalent Log-Normal Distribution

A log-normal distribution often allows for a highly accurate description of the size distribution of a polymer or particle sample:

$$PDF(G) = \frac{1}{G\gamma\sqrt{2\pi}}\exp\left[-\frac{(\ln G - \beta)^2}{2\gamma^2}\right] \quad (25.)$$

Where:

PDF(G) is the probability density that the particles of the sample will have a G value between G and G+dG; and, β and γ are respectively the average and the standard deviation of the logarithm of the parameter G, ln G.

Although the log-normal distribution may be a poor model for more complex mixtures, the determination of the equivalent log-normal distribution of any mixture is useful to estimate the interval of the values of the parameter G on which the distribution P(G) that is the solution of equation (6) is to be sought.

The probability density PDF (G) depends only on the parameters β and γ. It is possible to determine these two parameters from $\langle G \rangle_T$ and $\langle G \rangle_\Gamma$.

The definition is:

$$\langle G \rangle_T = \left[\int_0^\infty G^{-1} PDF(G) dG\right]^{-1} \quad (26.)$$

$$\langle G \rangle_\Gamma = \frac{\int_0^\infty G^{3/2} PDF(G) dG}{\int_0^\infty G^{1/2} PDF(G) dG} \quad (27.)$$

By replacing equation (27) in equations (28) and (29), the following is obtained:

$$\beta = \frac{1}{3}\ln\langle G \rangle_\Gamma + \frac{2}{3}\ln\langle G \rangle_T \quad (28.)$$

$$\gamma = \sqrt{\frac{2}{3}\ln\frac{\langle G \rangle_\Gamma}{\langle G \rangle_T}} \quad (29.)$$

It is also possible to obtain the equivalent log-normal distribution from first- and second-order cumulants according to the following relations:

$$\beta = \ln\Gamma_1 - \ln\left(1 + \frac{\Gamma_2}{\Gamma_1^2}\right) \quad (30.)$$

$$\gamma = \sqrt{\ln\left(1 + \frac{\Gamma_2}{\Gamma_1^2}\right)} \quad (31.)$$

In conclusion, it is possible to determine the log-normal distribution either from $\langle G \rangle$ and $\langle G \rangle_\Gamma$ according to equations (30) and (31) or from $\Gamma_1$ and $\Gamma_2$ using equations (32) and (33).

Calculation of the Limits of the Interval Based on the Equivalent Log-Normal Distribution The $G_{min}$ et $G_{max}$ may be estimated by replacing the distribution P(G) with an equivalent log-normal distribution.

The objective is for the interval $[G_{min}, G_{max}]$ to cover a significant fraction of the log-normal distribution equivalent to the experimental Taylor signal. This fraction of the distribution is yielded by:

$$\Delta Q_G = Q_G(G_{max}) - Q_G(G_{min}), \quad (32.)$$

where $Q_G(G)$ is the cumulative probability defined by:

$$Q_G(G) = \int_0^G dG' PDF(G'). \quad (33.)$$

Furthermore, it is preferable for the interval $[Q_G(G_{min}), Q_G(G_{max})]$ to be distributed symmetrically relative to the median value $Q_G=\frac{1}{2}$. Thus:

$$Q_G(G_{min}) = 1 - Q_G(G_{max}) \quad (34.)$$

In the context of this assumption, equation (36) yields:

$$erf\left(\frac{\ln G_{max} - \beta}{\sqrt{2}\gamma}\right) = 2Q_G(G_{max}) - 1 = \Delta Q_G \quad (35.)$$

where erf is the error function known to persons skilled in the art.

This results in:

$$G_{max} = \beta + k\sqrt{2}\gamma \text{ i.e., } G_{max} = \exp(\beta + k\sqrt{2}\gamma); G_{max} = \exp(\beta + k\sqrt{2}\gamma), \quad (36.)$$

and $$G_{min} = \beta - k\sqrt{2}\gamma \text{ i.e., } G_{min} = \exp(\beta - k\sqrt{2}\gamma); G_{min} = \exp(\beta - k\sqrt{2}\gamma), \quad (37.)$$

with $k = erf^{-1}(\Delta Q_G)$ where $erf^{-1}$ is the inverse error function.

For example, if $\Delta Q_G = 99.53\%$, then k=2, or if $\Delta Q_G = 99.998\%$, then k=3.

Empirical Determination of the Interval Based on the Breakdown into Cumulants

For the sake of simplicity, the following notation will be used: $x=(t-t_0)^2$.

For a monodispersed sample, ln [s(t)] as a function of x is a line, the gradient of which gives the diffusion coefficient of the species of the sample. That is:

$$\left|\frac{\partial \ln s}{\partial x}\right| = G \qquad (38.)$$

Thus, $\partial \ln s/\partial x$ does not depend on x, i.e., it is not time-dependent.

On the other hand, for a polydispersed sample, the curve ln [s(t)] depending on x has a curve that is calculated by determining the derivative $\partial \ln s/\partial x$. This is proportional to the parameter G.

Based on equation (40), it is assumed that $G_{min}$ is linked to the minimum of the local gradient of ln s (in absolute value), because the species with low diffusion coefficients correspond to low G values, and thus to a slight decrease of the Taylor signal over time. Accordingly, it is assumed that:

$$G_{min} = b_{min}\left|\frac{\partial \ln s}{\partial x}\right|_{min} \qquad (39.)$$

where the minimum of $|\partial \ln s/\partial x|$ sought on an adapted interval of x, to be determined empirically, and where $b_{min}$ is a numerical coefficient, also to be determined empirically.

By studying a large number of Taylor signals of samples of all kinds, we have found that the suitable interval of x is that for which the signal s(t) decreases by two decades. This corresponds to an interval in time between the time $t_0$ corresponding to the peak of s(t) and the time $t_1$ such that $s(t_1)=S(t_1)/S(t_0)=0.01$.

Likewise, it is considered that:

$$G_{max} = b_{max}\left|\frac{\partial \ln s}{\partial x}\right|_{max} \qquad (40.)$$

where the maximum of $|\partial \ln s/\partial x|$ is sought on the same interval of x.

In analysing an experimental Taylor signal, it is simpler to estimate the characteristic decrease time of s(t). Defining the decrease time as $\tau=G^{-1/2}$, minimum and maximum decrease times are defined based on the aforementioned relations, according to:

$$\tau_{min} = a_{min}\left(\left|\frac{\partial \ln s}{\partial x}\right|_{max}\right)^{-1/2} \qquad (41.)$$

$$\tau_{max} = a_{max}\left(\left|\frac{\partial \ln s}{\partial x}\right|_{min}\right)^{-1/2} \qquad (42.)$$

By studying a large number of Taylor signals of samples of all kinds, we have found that the following values of the parameters $\alpha_{min}$ and $\alpha_{max}$ are able to frame the desired min and max values.

$$\alpha_{min}=0.1; \alpha_{max}=3 \text{ i.e., } b_{min}=1/9; b_{max}=100 \qquad (43.)$$

Lastly, the values $G_{min}$, $G_{max}$ to use in order to adjust the data are calculated according to:

$$G_{min} = \tau_{max}^{-2} \qquad (44.)$$

$$G_{max} = \tau_{min}^{-2} \qquad (45.)$$

Calculation of the Distributions According to the Parameter D, $R_h$, or M Based on the Distribution According to the Parameter G Once the distribution of the amplitudes P(G) has been obtained, the distribution of the amplitudes $P_D(D)$ according to the diffusion coefficient D, can be easily calculated.

The following equation links the probability distribution $P_y$ of the stochastic variable y to the probability distribution $P_x$ of the stochastic variable x, where x is a function of y:

$$P_y(y) = P_x(x)|_{x=x(y)} \left|\frac{\partial x}{\partial y}\right|_{x=x(y)} \qquad (46.)$$

with $G=12D/(R_c^2 t_0)$, the following is obtained:

$$P_D(D) = \frac{\frac{12}{R_c^2 t_0} P(G)\big|_{G=\frac{12D}{R_c^2 t_0}}}{\int_0^\infty P(G)dG} \qquad (47.)$$

In this expression, an integral was introduced to the denominator because the distribution P(G) is not necessarily normalized.

It is often desirable to express the polydispersity of the sample in terms of amplitude distribution according to the first hydrodynamic ray $R_h$, or the parameter of molar mass, M.

These two distributions may be calculated based on the distribution P(G) using equation (46) and the following transformation rules:

$$G = \frac{2k_B T}{\pi \eta R_c^2 t_0} R_h^{-1} \qquad (48.)$$

$$G = \frac{2k_B T}{\pi \eta R_c^2 t_0}\left(\frac{10\pi N_a}{3K}\right)^{1/3} M^{-\left(\frac{1+a}{3}\right)} \qquad (49.)$$

Equation (48) uses the Stokes-Einstein relation $$D = \frac{k_B T}{6\pi \eta R_h},$$

where $k_B$ is the Boltzmann constant, T the absolute temperature, and $\eta$ the viscosity of the eluent.

Equation (49) uses the Einstein equation for the viscosity of a diluted suspension and the Mark Houwink equation linking the intrinsic viscosity $[\eta]$ to the molar mass according to the relation:

$$[\eta] = K M^a \qquad (50.)$$

where K and a are the Mark Houwink coefficients.

The following relation, which gives the hydrodynamic ray as a function of molar mass, may also be used:

$$R_h = \left(\frac{3K}{10\pi N_a}\right)^{1/3} M^{\left(\frac{1+a}{3}\right)} \quad (51.)$$

where $N_a$ is Avogadro's number and $d_f=3/(1+a)$ is the fractal dimension of the object (e.g., $d_f=3$ for an ordinary compact object, 2 for a statistical polymer, and 5/3 for a polymer in a good solvent).

Equations (48) and (49) show that G is non-linear in $R_h$ and M, respectively, whilst G is simply proportional to D.

Due to this non-linearity, the transformation of the distribution according to the parameter G identified as the solution of equation (6) results in a distribution according to the parameter $R_h$, or the parameter M, which does not necessarily observe the constraint of the cost function, in particular the regularity constraint. In most cases, the transform results in fact in the presence of non-physical peaks or oscillations in the distribution according to the parameter $R_h$, or the parameter M.

This is why, in a variant of the method described in detail above, the method consists of directly seeking the distribution according to the parameter $R_h$, or the parameter M, which observes the constraint(s) and allows for the correct reproduction of the experimental data, by constrained regularization.

To this end, the experimental Taylor signal is broken down on a family of Gaussians of an adapted parameter: The equation (5) is thus generalized in the form of:

$$\hat{S}(t) = \int_0^\infty P(G_{(c)}) G_{(c)}^{c/2} \exp[-(t-t_0)^2 G_{(c)}^c] dG, \quad (52.)$$

where the three following cases are considered:
1) c=1: to be used when seeking the amplitude distribution according to D;
2) c=−1: to be used when seeking the amplitude distribution according to $R_h$;
3) c=−1/$d_f$=−(1+a)/3: to be used when seeking the amplitude distribution according to M;

$P_{norm}(G_{(c)})$ is the distribution $P(G_{(c)})$, properly normalized:

$$P_{norm}(G_{(c)}) = \frac{P(G_{(c)})}{\int_0^\infty P(G_{(c)}) dG_{(c)}}. \quad (53)$$

In case 1), $G_{(f)}=G$. Equation (54) then reduces to equation (5). The amplitude distribution $P_D(D)$ is determined based on the amplitude distribution $P(G_{(1)})$ using the following equation:

$$P_D(D) = \frac{12}{R_c^2 t_0} P_{norm}(G_{(1)}). \quad (54.)$$

For case 2), $$G_{(-1)} = \frac{\pi \eta R_c^2 t_0}{2 k_B T} R_h.$$

The implementation of the constrained regularization algorithm results in the determination of the amplitude distribution $P(G_{(-1)})$. The distribution $P_R(R_h)$ is then determined based on $P_{norm}(G_{(-1)})$ according to the relation:

$$P_R(R_h) = \frac{\pi \eta R_c^2 t_0}{2 k_B T} P_{norm}(G_{(-1)}). \quad (55.)$$

Lastly, for case 3), $$G_{(-(1+a)/3)} = \left(\frac{3K}{10\pi N_a}\right)^{\left(\frac{1}{1+a}\right)} \left(\frac{\pi \eta R_c^2 t_0}{2 k_B T}\right)^{\left(\frac{3}{1+a}\right)} M.$$

The implementation of the constrained regularization algorithm results in the determination of the amplitude distribution $P(G_{(-(1+a)/3)})$. The distribution $P_M(M)$ is then determined by means of $P_{norm}(G_{(-(1+a)/3)})$ according to the following relation:

$$P_M(M) = \left(\frac{3K}{10\pi N_a}\right)^{\left(\frac{1}{1+a}\right)} \left(\frac{\pi \eta R_c^2 t_0}{2 k_B T}\right)^{\left(\frac{3}{1+a}\right)} P_{norm}(G_{-1((1+a)/3)}). \quad (56)$$

The manner of selecting the interval $[G_{(c),min}, G_{(c),max}]$ on which the distribution $P(G_{(c)})$ is to be sought is similar to that described above. In particular, $\tau_{min}$ and $\tau_{max}$ are calculated according to equations (43) and (44). Lastly, the values $G_{(c),min}, G_{(c),max}$ are determined as follows:

1) $c = 1$: $G_{min} = \tau_{max}^{-2}$, $G_{max} = \tau_{min}^{-2}$. (57)

2) $c = 1$ $G_{min} = \tau_{max}^2$, (58)
$G_{max} = \tau_{min}^2$.

3) $c = -1/d_f = -(1+a)/3$ $G_{min} = \tau_{max}^{\left(\frac{6}{1+a}\right)}$, (59)
$G_{max} = \tau_{min}^{\left(\frac{6}{1+a}\right)}$.

Method for Determining the Size Distribution of a Sample

Figure 2:
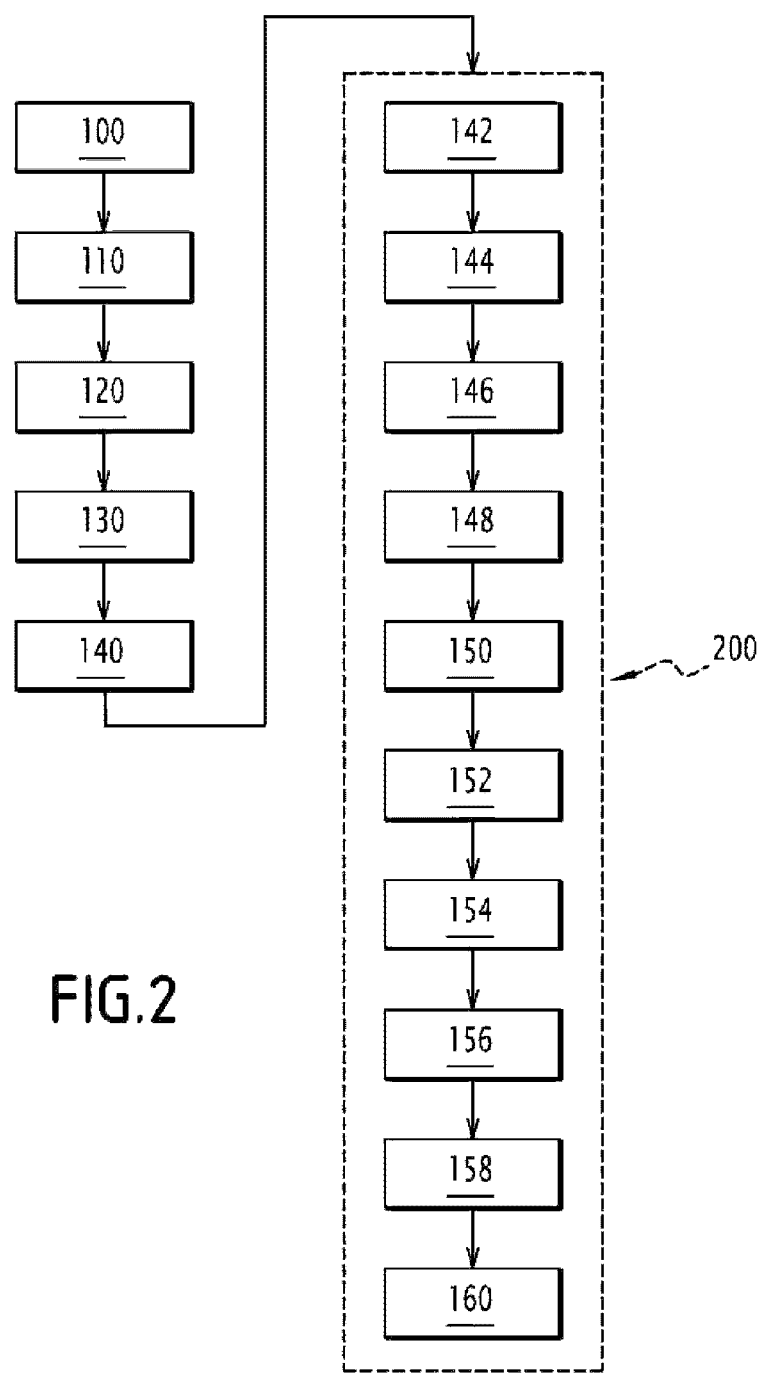
FIG. 2 is a schematic block representation of the method for determining the size distirbution of a particle mixture implemented by the system of FIG. 1.

The method for determining the size distribution of a mixture of particles will now be described by reference to FIG. 2.

The method includes a first step 100 of injecting a sample to be analyzed into the injection section 7 of the experimental device 3.

Then, in step 110, after actuating the means 13 for introducing and circulating an eluent inside the capillary 6, the sample injected is transported from the injection section 7 to the detection section 9 of the experimental device 3. The experimental conditions (nature of the eluent, flow speed of the eluent, transport distance separating the injection section from the detection section, temperature, internal ray of the capillary, etc.) are adapted so that a Taylor dispersion phenomenon will occur that is detectable in the detection section 9. In the experimental examples below, precise experimental conditions are indicated.

In step 120, the sample transported by the eluent passes through the optical cell of the detection section 9. The sensor 17 then generates an electrical measurement signal characteristic of the Taylor dispersion occurring in the sample.

In step 130, the detection signal generated by the sensor 17 is processed by the electronic card 19 so as to deliver a digitized experimental Taylor signal $\hat{S}(t)$.

In step 140, the experimental Taylor signal $\hat{S}(t)$ is acquired by the computer 5.

It is then analyzed (step 200) by running the software 31 in order to determine a size distribution. The software 31 carries out the following elementary steps.

In step 142, a first adapted menu is presented to the user so that the user may select the parameter according to which the constrained regularization method is to be carried out. The user may thus choose either the diffusion coefficient D (case 1, c=1), the hydrodynamic ray (case 2, c=−1), or the molar mass M (case 3, c=−1/$d_f$). The user is also asked to choose the number N for the discretization of the distribution sought. In the following, for simplicity, it is assumed that the user chooses the diffusion coefficient D and that the parameter to be taken into account is the parameter G.

In step 144, a second adapted menu is presented to the user so that the user may select the number and nature of the constraints to be taken into account in seeking the distribution that is the solution of equation (5). The proposed constraints to select are, e.g.:
1. regularity of distribution;
2. the distribution is positive at all points;
3. the distribution must result in a predetermined T average plus or minus a deviation to be specified;
4. the distribution must result in a predetermined r average plus or minus a deviation to be specified.

In the following, it is assumed that the first constraint is implemented via a Lagrange multiplier in the cost function, whilst the other constraints are implemented directly by appropriately limiting the space of the amplitudes $P(G_m)$ in which an extrema of the cost function is sought.

In step 146, the experimental Taylor signal $\hat{S}(t)$ is broken down into cumulants. More specifically, the normalized Taylor signal $s(t)=\hat{S}(t)/\hat{S}(t_0)$ is first determined, then its logarithm ln [s(t)] is calculated. Lastly, a second-degree polynomial of the variable $(t-t_0)^2$ is adjusted to the function ln [s(t)]. The first- and second-order cumulants $\Gamma_1$ and $\Gamma_2$ are then determined. $\Gamma_1$ allows, in particular, for a measurement of the $\Gamma$ average of the parameter G. Additionally, the T average of the Taylor signal is measured.

In step 148, the limits $G_{min}$ and $G_{max}$ of the interval of the values of the parameter G on which the distribution is sought are calculated based on the equivalent log-normal distribution determined based on the values of the first- and second-order cumulants $\Gamma_1$ and $\Gamma_2$ obtained in step 148, using equations (32) and (33) followed by (38) and (39).

In step 150, the cost function $H_\alpha$ is developed from the first constraint selected by the user in step 144. The constraint term associated with the constraint selected is red in the memory of the computer 5.

In step 152, the discretized expression of the cost function $H_\alpha$ is obtained by subdividing the interval $G_{min}$ and $G_{max}$ determined in step 154 into N sub-intervals.

In step 154, for each value of the Lagrange coefficient $\alpha$ in a group of test values, the minimum of the cost function $H_\alpha$ is determined. To take into account strict constraints according to which the amplitudes are positive and must result in predetermined T and $\Gamma$ averages with a predetermined deviation, the minimum of the cost function is sought exclusively on the appropriate subspace of the amplitudes $P(G_m)$ that satisfy these strict constraints.

In step 156, the statistical error ν is determined, and the optimal value $\alpha_0$ of the Lagrange coefficient α is determined by selecting the value of the Lagrange coefficient α, which, in step 156, resulted in the nearest distance term $\chi_2$ by values lower than this statistical error ν.

In step 158, the group of distributions P(G) sought is the group of those that minimise the cost function $H_\alpha$ for the optimal value $\alpha_0$ of the Lagrange coefficient determined in step 156.

In step 160, the value related to the size of the particles of the mixture is calculated based on the distribution P(G) obtained in step 158.

Lastly, in step 162, for an adapted transformation, the distributions according to the hydrodynamic ray or molar mass are calculated based on the distribution P(G) obtained in step 158.

If applicable, the various distributions calculated are displayed on the screen of the computer 5. The software 31 includes 'tools' allowing the user to carry out the desired calculations on the calculated distributions.

The software 31 thus includes means suited for the execution of each of the steps of the analysis of the experimental Taylor signal.

In one variant, the limits $G_{min}$ and $G_{max}$ of the interval on which the distribution P(G) is sought are calculated empirically. This consists of determining the normalized Taylor signal $s(t)=\hat{S}(t)/\hat{S}(t_0)$, obtaining its logarithm, and then calculating the derivative $|\partial \ln s/\partial x|$. The limits of the interval of interest of the parameter G are finally deduced using equations (43) and (44), followed by equations (46) and (47).

In yet another variant, independent of the preceding variant, the T average of the parameter G, $\langle G \rangle_T$, is calculated by integrating the experimental Taylor signal $\hat{S}(t)$ using equation (16), and the $\Gamma$ average of the parameter G, $\langle G \rangle_\Gamma$, is calculated based on the determination of the first-order cumulant resulting from the breakdown of the experimental Taylor signal into cumulants. The limits $G_{min}$ and $G_{max}$ of the interval on which the size distribution is to be sought are calculated based on the T and $\Gamma$ of the parameter G according to equations (30), (31), and (38), (39). This variant of the method also allows for a constraint term based on one or the other of these averages to be integrated into the cost function.

Constrained Regularization Analysis on a Series of Experimental Taylor Signals of a Single Sample Adjustment by constrained regularization may be advantageously implemented using several experimental Taylor signals obtained by repeating identical experiments on a group of samples of a single mixture.

Although each repetition may be analyzed independently, and the amplitude distributions obtained may be averaged, it has been found to be more robust to accumulate the various individual Taylor signals into a single global Taylor signal including a number of experimental points equal to the sum of the experimental points of each individual Taylor signal. Secondly, the amplitude distribution is sought on the global Taylor signal by applying the constrained regularization algorithm.

This results in an amplitude distribution P(G) that most closely observes the constraint imposed, e.g., the distribution P(G) is more regular. This also allows the uncertainties and imprecisions affecting the acquisition of the individual Taylor signals to be taken into account.

During this operation, if the reference time $t_0$ is not strictly identical from one experimental Taylor signal to another, the time coordinates are translated such that all experimental Taylor signals have exactly the same reference time $t_0$.

The correction of the baseline, followed by the normalization of each experimental Taylor signal, may also be necessary before processing.

The software 31 includes a menu allowing users to process several experimental Taylor signals before analysing the global Taylor signal thus obtained.

Advantages

The method just discussed allows the size distribution of a mixture of species, as well as the concentrations of these species in the mixture, to be obtained automatically and in real time, no matter what the polydispersity of the sample analyzed is, i.e., the number of species included in this sample and the respective concentrations thereof.

The fields of application of the device and method described above include the size characterization of polymers, colloids, latex nanomaterials, emulsions, liposomes, vesicles, and molecules or biomolecules in general. One important field of application is the study of the stability/degradation/aggregation of proteins for the pharmaceuticals industry.

The advantages of the characterization of a sample by means of the Taylor dispersion phenomenon are known to persons skilled in the art: Low volume of the sample to be injected into the capillary, no need to calibrate the experimental device, use of an extremely simple experimental device, technique that is particularly well adapted to size measurements of particles smaller than a few nanometers, a signal that is generally sensitive to mass concentration, etc.

EXPERIMENTAL EXAMPLES

Experimental Conditions

Virgin silicon capillary: $R_c$=50 μm with a distance between the injection and detection sections of 30 cm.
Temperature: T=293° K
Eluent: Sodium borate buffer 80 mM, pH 9.2.
Viscosity of the eluent: $\eta$=8.9 $10^{-4}$ Pa·s.
Sample: Polystyrene sulphonate (PSS) 0.5 g/l.
Injection: 0.3 psi (20 mbar), 9 s, i.e., an injected volume of 8 nl (total capillary volume 589 nl).
UV detection at a wavelength of 200 nm.

Characteristics of the Polymer Standards Injected

1) PSS 1290    $M_w$ = 1290 g/mol    $M_p$ = 1094 g/mol    $M_w/M_n$ < 1.20
2) PSS 1590    $M_w$ = 5190 g/mol    $M_p$ = 5280 g/mol    $M_w/M_n$ < 1.20
3) PSS 29000   $M_w$ = 29000 g/mol   $M_p$ = 29500 g/mol   $M_w/M_n$ < 1.20
4) PSS 148000  $M_w$ = 145000 g/mol  $M_p$ = 148500 g/mol  $M_w/M_n$ < 1.20
5) PSS 333000  $M_w$ = 333000 g/mol  $M_p$ = 338000 g/mol  $M_w/M_n$ < 1.20 where $M_w$ is the average molar mass by weight, $M_p$ the molar mass at the summit of the chromatographic peak, and $M_w/M_n$ is the polydispersity index. The average molar masses and the characteristics of the distribution were given by the supplier, who determines them by steric exclusion chromatography with calibration using polymer standards of the same chemical nature (PSS).

Experimental Taylor Signals of the Polymers Studied

Figure 3:
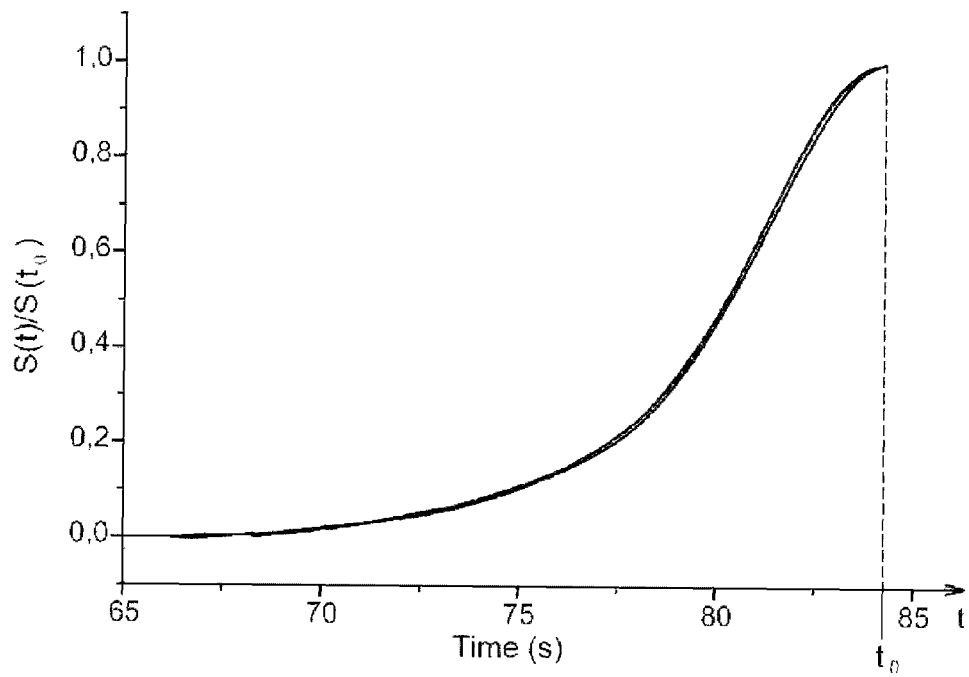
FIGS. 3-5 (A and B) are graphs showing the results of the implementation of the method of FIG. 2 in the case of an equimassic mixture of two samples of synthetic polymers.

FIG. 3 shows an experimental Taylor signal obtained for an equimassic mixture of PSS 1290 and PSS 29000. In fact, three experimental Taylor signals are aggregated here.

Furthermore, only the left part of the experimental Taylor signal is shown. In fact, generally, taylorgrams are symmetrical. However, in the case of the phenomenon of adsorption to the capillary surface, the right part of the signal, corresponding to the times following the time $t_0$, may not be exactly symmetrical on the left part of the signal, corresponding to the time preceding the time $t_0$. In this case, it is preferable to focus the processing of the data on the left part of the experimental Taylor signal. Advantageously, the method described above only takes into account the left part of the signal in order to limit the influence of these possible parasitic phenomena.

Figure 4:
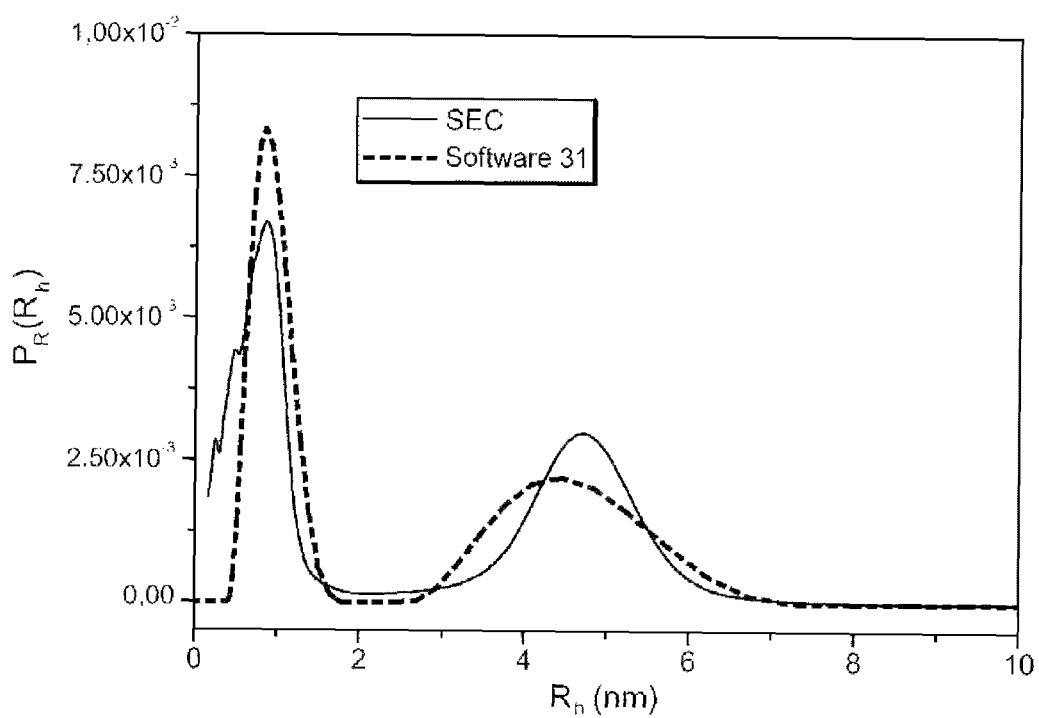

FIG. 4 shows the superimposition of the distribution $P_R(R_h)$ obtained by the aforementioned method (software 31) compared to the distribution given by the supplier of the polymers and obtained by a chromatographic method (SEC). FIG. 4 shows good consistency between the hydrodynamic ray distribution given by the supplier and the distribution obtained by running the software 31.

Figure 5:
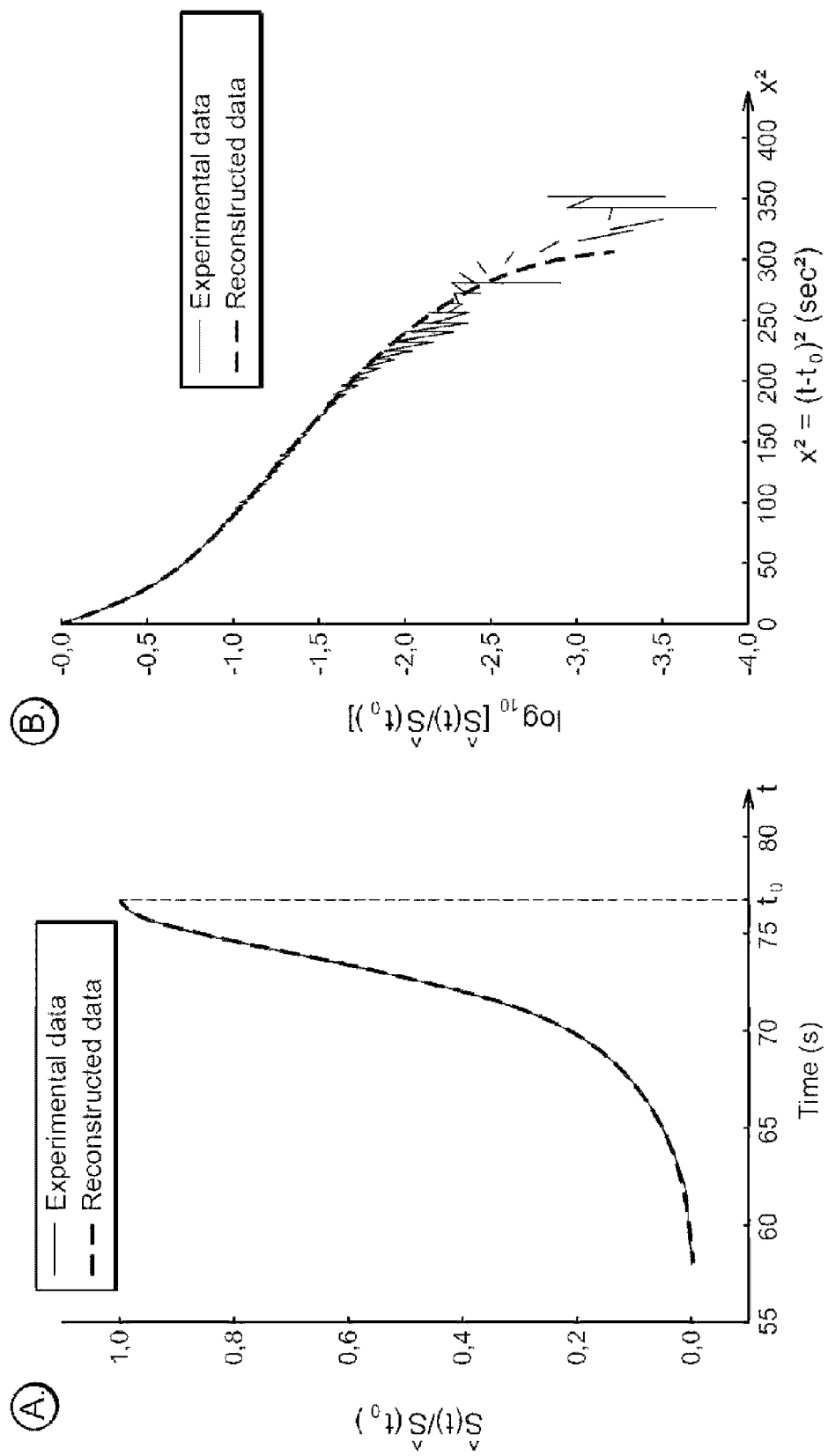

FIG. 5A shows the adjustment between the normalized experimental Taylor signal $\hat{S}(t)$ (Data) and the normalized reconstructed signal $S'(t)$ (Fit), and FIG. 5B shows the adjustment between the logarithm of the normalized experimental Taylor signal $\hat{S}(t)$(Data) and the cumulant development (Fit).

Comparison of the Results

Table 1 shows the various averages of the diffusion coefficient D obtained: Directly by breakdown into cumulants (Γ average, column 2) or by integrating the taylorgram (τ average, column 3), and, on the other hand, by running the software 31 (Γ average, column 4 and τ average, column 5). It should be noted that, in this example, the averages measured directly on the experimental Taylor signal are not used to constrain the deconvolution of the signal, and only a loose regularity constraint and a strict positivity constraint were used.

TABLE 1

| 1 Sample: | 2 $\langle D \rangle_\Gamma{}^a$ | 3 $\langle D \rangle_\tau{}^b$ | 4 $\langle D \rangle_\Gamma{}^c$ | 5 $\langle D \rangle_\tau{}^c$ |
|---|---|---|---|---|
| 1290 | 2.534E−06 | 2.457E−06 | 2.654E−06 | 2.595E−06 |
| 5190 | 1.197E−06 | 1.083E−06 | 1.197E−06 | 1.192E−06 |
| 29000 | 4.754E−07 | 4.222E−07 | 5.152E−07 | 5.135E−07 |
| 145000 | 2.014E−07 | 1.899E−07 | 2.218E−07 | 2.201E−07 |
| 333000 | 1.209E−07 | 1.157E−07 | 1.413E−07 | 1.119E−07 |
| 1290 + 29000 | 1.065E−06 | 8.407E−07 | 1.900E−06 | 8.533E−07 |
| 1290 + 5190 | 2.137E−06 | 1.555E−06 | 2.082E−06 | 1.812E−06 |
| 5190 + 29000 | 7.669E−07 | 6.509E−07 | 9.237E−07 | 6.921E−07 |

[a] based on the breakdown into cumulants (equation 25)
[b] based on the integration of the taylorgram (equation 17)
[c] based on the distribution given by the software 31

Overall, the results show great coherence, and the software 31 results in a solution in which the T and Γ averages (columns 4 and 5) are close to the experimental values (columns 2 and 3).

Table 2 shows the values of $\tau_{min}$ and $\tau_{max}$ determined based on the various proposed approaches, i.e., the imperical approach (columns 4 and 5), breakdown into cumulants (columns 6 and 7) based on the cumulants $\Gamma_1$ and $\Gamma_2$ (columns 2 and 3), and the approach using the T and Γ averages of the diffusion coefficient (columns 8 and 9 based on the first-order cumulant and the integration of the taylorgram).

The time at peak $t_0$ affects both a cumulant analysis and the determination of the size distribution obtained by constrained regularization.

Additionally, the cumulant method is based on a limited development for $(t-t_0) \to 0$. From an experimental standpoint, it is necessary to choose the range of time t for the analysis wisely: If one limits oneself to a very small interval, the result will be substantially affected by measurement noise. If, on the other hand, too wide an interval is considered, the contribution of the higher-order $(t-t_0)$ terms, which are ignored in the cumulant method, will be significant.

TABLE 2

| 1 Sample: | 2 $\Gamma_1$ $s^{-2}$ | 3 $\Gamma_2$ $s^{-4}$ | $4^a$ $\tau_{min}/\alpha_{min}$ $s^a$ | $5^a$ $\tau_{max}/\alpha_{max}$ $s^a$ | $6^b$ $\tau_{min}/\alpha_{min}$ $s^b$ | $7^b$ $\tau_{max}/\alpha_{max}$ $s^b$ | $8^c$ $\tau_{min}/\alpha_{min}$ en s | $9^c$ $\tau_{max}/\alpha_{max}$ en s |
|---|---|---|---|---|---|---|---|---|
| 1290 | 6.339E−02 | 1.231E−05 | 3.891 | 4.280 | 3.679 | 4.301 | 3.277 | 4.914 |
| 5190 | 3.004E−02 | 5.638E−06 | 5.554 | 5.985 | 5.176 | 6.471 | 4.137 | 8.603 |
| 29000 | 1.189E−02 | 6.307E−06 | 7.595 | 9.052 | 6.975 | 12.593 | 6.408 | 14.203 |
| 145000 | 5.038E−03 | 1.651E−06 | 9.804 | 13.555 | 10.195 | 20.736 | 10.856 | 19.016 |
| 333000 | 3.024E−03 | 5.378E−07 | 11.279 | 30.264 | 13.344 | 26.235 | 14.497 | 23.480 |
| 1290 + 29000 | 2.664E−02 | 8.047E−05 | 4.704 | 8.860 | 4.067 | 10.276 | 3.781 | 11.622 |
| 1290 + 5190 | 5.210E−02 | 2.518E−04 | 4.453 | 7.740 | 3.005 | 6.978 | 2.540 | 9.343 |
| 5190 + 29000 | 1.918E−02 | 2.571E−05 | 6.625 | 9.891 | 5.171 | 10.784 | 4.777 | 12.172 |

$^a$empirical approach based on equations (43) and (44)
$^b$based on the cumulant breakdown (equations (32-33), (38-39), and (46-47))
$^c$based on the T and Γ averages of the diffusion coefficient (equations (17), (25), (30-31), (38-39), and (46-47)).

The orders of magnitude of $\tau_{min}$ and $\tau_{max}$ are highly consistent no matter what method is considered.

Table 3 compares the average hydrodynamic ray values obtained by breakdown into cumulants (Γ average, column 2), and by running the software 31 by determining the distribution P(G) followed by the Γ T integration (columns 3 and 6), by the reference method by steric exclusion chromatography (columns 4 and 7) following the average in question, by direct integration of the taylorgram on the entire signal (column 5). For the same average (columns 2-4, on the one hand, and column 5-7, on the other hand), the results are homogeneous for all samples considered.

This shows high consistency for all samples for each group of averages in question.

A step for determining a peak time $t_0$, as well as an optimal range of times suitable to a cumulant analysis, is shown below.

In a first sub-step, a first estimate $t_{0,guess}$ of the peak time is obtained, e.g., by considering the time for which $\hat{S}(t)$ is at its maximum or by adjusting the peak of $\hat{S}(t)$ by means of a parabolic or Gaussian function.

In a second sub-step, a list of N peak times to be tested $t_{0,i}$ is established, with the natural integer i varying between 1 and N, where the times $t_{0,i}$ are around $t_{0,guess}$ and regularly spaced by a constant time increment, with:

$t_{0,1} < t_{0,2} < \ldots t_{0,N}$;

$t_{0,i+1} = t_{0,i} + dt$; and $t_{0,1} = t_{0,guess} - \Delta t, t_{0,N} = t_{0,guess} + \Delta t$;

TABLE 3

| 1 Sample: | 2 $\frac{kT}{6\pi\eta[\langle D \rangle_\Gamma]_{cumulant}}$ | 3 $\frac{kT}{6\pi\eta[\langle D \rangle_\Gamma]_{log\ iciel31}}$ | 4 $\frac{kT}{6\pi\eta[\langle D \rangle_\Gamma]_{SEC}}$ | 5 $\frac{kT}{6\pi\eta[\langle D \rangle_T]_{Taylor}}$ | 6 $\frac{kT}{6\pi\eta[\langle D \rangle_T]_{Logiciel31}}$ | 7 $\frac{kT}{6\pi\eta[\langle D \rangle_T]_{SEC}}$ |
|---|---|---|---|---|---|---|
| 1290 | 0.968 | 0.924 | $0.913^a$ | $0.998^b$ | $0.945^c$ | $1.000^d$ |
| 5190 | 2.049 | 2.048 | 1.880 | 2.265 | 2.057 | 1.989 |
| 29000 | 5.159 | 4.761 | 5.076 | 5.810 | 4.776 | 5.278 |
| 145000 | 12.178 | 11.057 | 12.200 | 12.917 | 11.144 | 13.133 |
| 333000 | 20.286 | 17.359 | 17.297 | 21.190 | 21.917 | 20.915 |
| 1290 + 29000 | 2.303 | 1.291 | 1.319 | 2.917 | 2.874 | 3.449 |
| 1290 + 5190 | 1.148 | 1.178 | 1.046 | 1.578 | 1.354 | 1.470 |
| 5190 + 29000 | 3.198 | 2.655 | 2.473 | 3.768 | 3.544 | 3.638 |

$^a$obtained based on the distribution obtained by SEC.
$^b$obtained by integrating the taylorgram (based on the variance of the taylorgram).
$^c$obtained by integrating the weight distribution of the diffusion coefficients obtained by the software 31 (minimisation on D).
$^d$obtained based on the weight distribution of the hydrodynamic rays originating from the SEC.

Determination of the Time at the Peak

Experimentally, the time at the peak to of the experimental Taylor signal $\hat{S}(t)$ is not known with precision due to the measurement noise.

where dt is the time increment between two consecutive tested peak times; and

Δt is a time interval typically on the order of $t_{0,guess}/50$.

In a third sub-step, for each of the peak times to be tested $t_{0,i}$, a series of cumulant analyses is carried out taking into account various ranges of time of differing lengths.

The time range is, e.g., at a cutoff level of the signal $\hat{S}(t)$. For example, for a cutoff level of 0.1, the time range t is considered such that $\hat{S}(t) > 0.1 \times \hat{S}(t_{0,i})$. The value of the first and second cumulant resulting from the adjustment on each range of time is noted.

In a fourth sub-step, the optimal peak time $t_0$ is determined as being between the peak times for which the first cumulant $\Gamma_1$ diverges towards positive values when the cutoff level increases, and those for which the first cumulant $\Gamma_1$ diverges towards negative values when the cutoff level increases.

Tracing on a graph, for each peak time to be tested $t_{0,i}$, the curve of the first cumulant $\Gamma_1$ as a function of the cutoff level, the optimal peak time $t_0$ is that for which the curve is located between upward concave curves and downward concave curves. This curve has a smaller variation than the others.

The choice of optimal peak time is made by visual analysis of the aforementioned graphics or automatically, e.g., based on the sign of the second numerical derivative of the first cumulant $\Gamma_1$ as a function of the cutoff.

Alternatively or optimally, it is possible to do the same with the second cumulant $\Gamma_2$ and/or the square of the ratio of the second cumulant to the first cumulant. By doing it simultaneously for the first cumulant, the second cumulant, and the square of the ratio of the second cumulant to the first cumulant, the choice of peak time may be made more reliable.

In a fifth step, the optimal cutoff value is determined as the one that is the highest before the data show a significant deviation relative to their general tendancy due to the influence of measurement noise for very high cutoff levels.

The invention claimed is:

1. Method for determining the size distribution of a mixture of molecule or particle species comprising the following steps:

injecting a sample of the mixture to be analyzed inside a capillary in which an eluent is flowing;

transporting the sample injected along the capillary from an injection section to a detection section thereof, in experimental conditions suitable to generate a Taylor dispersion phenomenon that is measurable at the level of the detection section;

generating, by means of a suitable sensor included in the detection section, a signal characteristic of the Taylor dispersion of the transported sample;

processing the detection signal in order to obtain an experimental Taylor signal $\hat{S}(t)$; and analyzing the experimental Taylor signal $\hat{S}(t)$, wherein the step of analyzing an experimental Taylor signal $\hat{S}(t)$ of a sample of the mixture consists of searching an amplitude distribution $P(G_{(c)})$ that allows the experimental Taylor signal $\hat{S}(t)$ to be broken down into a sum of Gaussian functions by means of the equation I:

$$\hat{S}(t) = \int_0^\infty P(G_{(c)}) G_{(c)}^{c/2} \exp[-(t-t_0)^2 G_{(c)}^c] dG_{(c)} \quad (I)$$

where t is a variable upon which the experimental Taylor signal depends and $t_0$ is a value of the variable t common to the various Gaussian functions and corresponding to the peak of the experimental Taylor signal $\hat{S}(t)$;

$G_{(c)}$ is a characteristic parameter of a Gaussian amplitude function $P(G_{(c)})$ and is associated:

where c=1, with the diffusion coefficient D of a species according to the relation $$G_{(1)} = 12D/(R_c^2 t_0)$$

for c=−1, to the hydrodynamic ray $R_h$ of a species according to the relation $$G_{(-1)} = \frac{2k_B T}{\pi \eta R_c^2 t_0} R_h^{-1};$$

and for $c=-1/d_f=-(1+a)/3$, to the molar mass M of a species according to the relation $$G = \frac{2k_B T}{\pi \eta R_c^2 t_0} \left(\frac{10\pi N_a}{3K}\right)^{1/3} M^{-\left(\frac{1+a}{3}\right)},$$

where $k_B$ is the Boltzmann constant, T is the absolute temperature expressed in Kelvins at which the experiment is conducted, $\eta$ is the viscosity of the eluent used, $R_c$ is the internal ray of the capillary used, $N_a$ is Avogadro's number, and K and a are Mark Houwink coefficients, by implementing a constrained regularization algorithm consisting of minimizing a cost function $H_\alpha$ including at least one constraint term associated with a constraint that must observe the amplitude distribution $P(G_{(c)})$ that is the solution of the foregoing equation, whereby the minimization is carried out on an interval of interest of the values of the parameter $G_{(c)}$.

2. Method according to claim 1, wherein equation I is discretized by subdividing the interval of values of the parameter $G_{(c)}$, whereby each discretization point $G_m$ is indexed by an integer m that varies between the unit value and the value N, whereby the point $G_m$ is at a distance from the point $G_{m-1}$ corresponding to a sub-interval of the length $c_m$.

3. Method according to claim 2, wherein the cost function takes the following form:

$$H_\alpha = \chi^2 + \alpha^2 \Delta^2$$

where:

the first term $\chi^2$ is a distance term between the experimental Taylor signal $\hat{S}(t)$ and a reconstructed Taylor signal defined by:

$$S(t) = \Sigma_{m=1}^N c_m P(G_m) \sqrt{G_m} \exp[-(t-t_0)^2 G_m], \text{ and}$$

the second term $\Delta^2$ is a constraint term associated with the at least one constraint that must observe the amplitude distribution P(G) that is the solution of the foregoing equation, whereby the second term is introduced by a Lagrange coefficient $\alpha$, allowing the contribution of the second term of the cost function $H_\alpha$ to be adapted to the first term.

4. Method according to claim 3, wherein the first term $\chi^2$ is a distance of the type 'least squares' taking the form:

$$\chi^2 = \Sigma_{k=1}^L (S'(t_k) - \hat{S}(t_k))^2$$

where the experimental Taylor signal $\hat{S}(t)$ and the reconstructed function $S'(t)$ are sampled over time, whereby each sample is indexed by an integer k varying between the unit value and the value L.

5. Method according to claim 3, wherein the at least one constraint that must be observed by the amplitude distribution P(G) that is the solution of the foregoing equation is a regularity constraint associated with a constraint term $\Delta^2$ preferably taking the form:

$$\Delta^2 = \Sigma_{m=2}^{N-1}[P(G_{m-1})-2P(G_m)+P(G_{m+1})]^2.$$

6. Method according to claim 3, wherein the analysis step includes a step of determining the optimal value $\alpha_0$ of the Lagrange coefficient $\alpha$ such that the value of the distance term $\chi^2$ corresponding to the minimum of the cost function $H_{\alpha=\alpha 0}$ is close by values lower than a statistical error $v$, preferably of the form $v=L-N$.

7. Method according to claim 3, wherein, because the interval of interest of the values of the parameter $G_{(c)}$ are delimited by a minimum $G_{min}$ and a maximum $G_{max}$, the method includes a step of determining the values of the minimum and maximum.

8. Method according to claim 7, comprising a step of breaking down a normalized Taylor signal s(t) associated with the experimental Taylor signal Ŝ(t) into components by the relation: $s(t)=S(t)/S(t_0)$, consisting of adjusting to the curve ln [s(t)] a second-order polynomial of the variable $(t-t_0)^2$ so as to determine the first-order components $\Gamma_1$ and second-order components $\Gamma_2$, and in that the step of determining the values of the minimum $G_{min}$ and maximum $G_{max}$ uses the equations:

$$\beta = \ln\Gamma_1 - \ln\left(1+\frac{\Gamma_2}{\Gamma_1^2}\right)$$

and $$\gamma = \sqrt{\ln\left(1+\frac{\Gamma_2}{\Gamma_1^2}\right)}$$

where $\beta$ and $\gamma$ are respectively the average and the standard deviation of the logarithm of the parameter G of a log-normal distribution, followed by, $G_{min}=\exp(\beta-k\sqrt{2}\gamma)$ and $G_{max}=\exp(\beta+k\sqrt{2}\gamma)$.

9. Method according to claim 7, wherein the step of determining the values of the minimum and maximum of the interval of interest is empirical and consists of:
determining a normalized Taylor signal s(t) associated with the experimental Taylor signal Ŝ(t) by the relation: $s(t)=S(t)/S(t_0)$,
calculating the logarithm ln [s(t)],
determining the derivative $$\frac{\partial \ln s}{\partial x}$$

relative to the variable $x=(t-t_0)^2$, and
determining the values of the parameters $\tau_{min}$ and $\tau_{min}$ related to the extrema of the derivative according to the relations:

$$\tau_{min} = a_{min}\left(\left|\frac{\partial \ln s}{\partial x}\right|_{max}\right)^{-1/2}$$

$$\tau_{max} = a_{max}\left(\left|\frac{\partial \ln s}{\partial x}\right|_{min}\right)^{-1/2}$$

with $a_{min}=0,1$; $a_{max}=3$,
determining the minimum $G_{min}$ and maximum $G_{max}$ using the equations:

for $c=1$: $G_{min}=\tau_{max}^{-2}, G_{max}=\tau_{min}^{-2}$, for $c=-1$: $G_{min}=\tau_{min}^{-2}, G_{max}=\tau_{max}^{-2}$, for $c=-1/d_f=-(1+a)/3$:

$$G_{min} = \tau_{min}^{\left(\frac{6}{1+a}\right)},$$

$$G_{max} = \tau_{max}^{\left(\frac{6}{1+a}\right)}.$$

10. Method according to claim 7, wherein the step of determining the values of the minimum $G_{min}$ and maximum $G_{max}$ uses the following equations:

$$\beta = \frac{1}{3}\ln\langle G\rangle_\Gamma + \frac{2}{3}\ln\langle G\rangle_T$$

$$\gamma = \sqrt{\frac{2}{3}\ln\frac{\langle G\rangle_\Gamma}{\langle G\rangle_T}}$$

then $G_{min}=\exp(\beta-k\sqrt{2}\gamma)$ and $G_{max}=\exp(\beta+k\sqrt{2}\gamma)$.

11. Method according to claim 1, comprising a step of measuring an average in T, $\langle G\rangle_T$, of the parameter $G_{(1)}$ based on the experimental Taylor signal and/or an average in $\Gamma$, $\langle G\rangle_\Gamma$, of the parameter $G_{(1)}$ based on the breakdown, whereby each average may be used in a constraint that must be observed by the amplitude distribution $P(G_{(1)})$ that is the solution of the foregoing equation.

12. Method according to claim 10, wherein the step of determining the values of the minimum $G_{min}$ and maximum $G_{max}$ uses the following equations:

$$\beta = \frac{1}{3}\ln\langle G\rangle_\Gamma + \frac{2}{3}\ln\langle G\rangle_T$$

$$\gamma = \sqrt{\frac{2}{3}\ln\frac{\langle G\rangle_\Gamma}{\langle G\rangle_T}}$$

then $G_{min}=\exp(\beta-k\sqrt{2}\gamma)$ and $G_{max}=\exp(\beta+k\sqrt{2}\gamma)$.

13. Method according to claim 1, comprising a step of determining a peak time of the experimental Taylor signal Ŝ(t), comprising the following sub-steps:
obtaining a first estimate $t_{0,guess}$ of the peak time,
carrying out, for several different peak times to be tested $t_{0,i}$ selected around the estimated peak time $t_{0,guess}$, a series of cumulant analyses considering several ranges of time of different lengths specified based on a cutoff level;
selecting an optimal peak time $t_0$ for which the first cumulant $\Gamma_1$, the second cumulant $\Gamma_2$, and/or the square of the ratio of the second cumulant to the first cumulant diverges towards positive values when the cutoff level increases, for which, respectively, the first cumulant $\Gamma_1$, the second cumulant, $\Gamma_2$ and/or the square of the ratio of the second cumulant to the first cumulant diverges towards negative values when the cutoff level increases.

14. Data storage medium, comprising instructions for the execution of a method for determining the hydrodynamic ray, diffusion coefficient, or molar mass distribution of a mixture of molecule or particle species according to claim 1, when the instructions are executed by a computer.

15. System configured to determine hydrodynamic ray, diffusion coefficient, or molar mass distribution of a mixture of molecule or particle species including a computer, whereby the computer is programmed to execute a method for determining the hydrodynamic ray, diffusion coefficient, or molar mass distribution of a mixture of molecule or particle species according to claim 1.

* * * * *

UNITED STATES PATENT AND TRADEMARK OFFICE
CERTIFICATE OF CORRECTION

PATENT NO. : 9,689,786 B2
APPLICATION NO. : 14/410019
DATED : June 27, 2017
INVENTOR(S) : Hervé Cottet et al.

It is certified that error appears in the above-identified patent and that said Letters Patent is hereby corrected as shown below:

In the Claims

In Column 26 at Line 50 (approx..), in Claim 3, change "$S(t) = \sum_{m=1}^{N} c_m P(G_m)\sqrt{G_m} \exp[-(t-t_0)^2 G_m]$," to --$S'(t) = \sum_{m=1}^{N} c_m P(G_m)\sqrt{G_m} \exp[-(t-t_0)^2 G_m]$--.

In Column 27 at Line 54 (approx.), in Claim 9, change the second instance of "$\tau_{min}$" to --$\tau_{max}$--.

In Column 28 at Line 1, in Claim 9, change "for c=1, $G_{min} = \tau_{max}^{-2}$, $G_{max} = \tau_{min}^{-2}$" to --for c=1, $G_{min} = \tau^{-2}_{max}$, $G_{max} = \tau^{-2}_{min}$--.

In Column 28 at Line 3 (approx.), in Claim 9, change "for c = -1, $G_{min} = \tau_{min}^{-2}$, $G_{max} = \tau_{max}^{-2}$" to --for c = -1, $G_{min} = \tau^{-2}_{min}$, $G_{max} = \tau^{-2}_{max}$--.

In Column 28 at Line 62, In Claim 13, change "cumulant, $\Gamma_2$" to --cumulant $\Gamma_2$,--.

In Column 28 at Line 66, In Claim 14, change "medium," to --medium--.

Signed and Sealed this
Thirteenth Day of February, 2018

Andrei Iancu
*Director of the United States Patent and Trademark Office*